United States Patent [19]

Axen

[11] 4,215,222
[45] Jul. 29, 1980

[54] 6-KETO PROSTAGLANDIN DERIVATIVES

[75] Inventor: Udo F. Axen, Plainwell, Mich.

[73] Assignee: The Upjohn Company, Kalamazoo, Mich.

[21] Appl. No.: 959,400

[22] Filed: Nov. 9, 1978

Related U.S. Application Data

[60] Division of Ser. No. 819,857, Jul. 28, 1977, Pat. No. 4,158,667, which is a continuation-in-part of Ser. No. 725,548, Sep. 22, 1976, abandoned, which is a continuation-in-part of Ser. No. 716,972, Aug. 23, 1976, abandoned, which is a continuation-in-part of Ser. No. 655,110, Feb. 4, 1976, abandoned.

[51] Int. Cl.² ............................................. C07C 177/00
[52] U.S. Cl. ................................. 560/53; 260/346.22; 260/410; 260/410.5; 260/410.9 R; 260/413; 562/459; 562/463
[58] Field of Search ................. 560/53; 562/459, 463; 260/410.5, 410, 410.9, 413

Primary Examiner—Paul J. Killos
Attorney, Agent, or Firm—Robert A. Armitage; Morris L. Nielsen

[57] ABSTRACT

Prostaglandin (PG$_1$) derivatives having (1) a 6-keto feature, for example

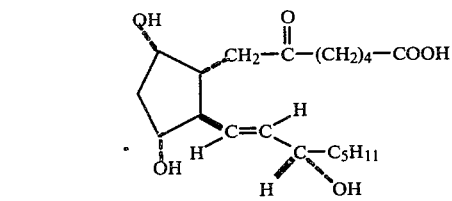

or (2) a 9-deoxy-6,9-epoxy feature together with a 5-halo or 6-hydroxy feature, for example

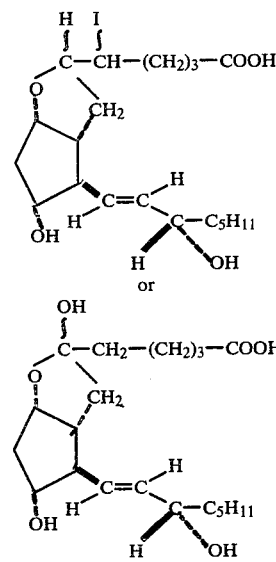

said derivatives having pharmacological activity. Processes for preparing them and the appropriate intermediates are disclosed.

145 Claims, No Drawings

6-KETO PROSTAGLANDIN DERIVATIVES

CROSS REFERENCE TO RELATED APPLICATIONS

This application is a division of copending application Ser. No. 819,857 filed July 28, 1977 issued as U.S. Pat. No. 4,158,667, which was a continuation-in-part of then copending application Ser. No. 725,548 filed Sept. 22, 1976, since abandoned, which was a continuation-in-part of then copending application Ser. No. 716,972 filed Aug. 23, 1976, since abandoned, which was a continuation-in-part of then copending application Ser. No. 655,110 filed Feb. 4, 1976, and since abandoned.

BACKGROUND OF THE INVENTION

This invention relates to prostaglandin derivatives and to a process for preparing them.

The prostaglandins and analogs are well-known organic compounds derived from prostanoic acid which has the following structure and atom numbering

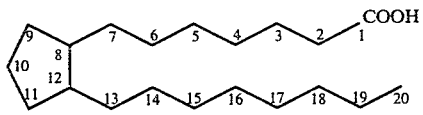

The essential material for this application, including the background of the invention, the disclosure of the invention, and the description of the preferred embodiments, including Preparations and Examples, is incorporated by reference from pending and commonly owned allowed U.S. application Ser. No. 819,857 filed July 28, 1977, for which the issue fee has been paid, now issued as U.S. Pat. No. 4,158,667 under the provisions of M.P.E.P. 608.01(p).

For background, see for example Bergstrom et al., Pharmacol. Rev. 20, 1 (1968) and Pace-Asciak et al., Biochem. 10, 3657 (1971). Subsequent to this invention there appeared a publication on 6-ketoprostaglandin $F_{1\alpha}$ by Pace-Asciak, J. Am. Chem. Soc. 98, 2348 (1976) and a publication on "PGX" (alternatively 6,9α-oxido-9α,15α-dihydroxyprosta(Z)5, (E)13-dienoic acid) by E. J. Corey et al., J. Am. Chem. Soc. 99, 2006 (1977).

SUMMARY OF THE INVENTION

It is the purpose of this invention to provide novel products having pharmacological activity. It is a further purpose to provide a process for preparing these products and their intermediates.

Accordingly, there is provided a compound of the formula:

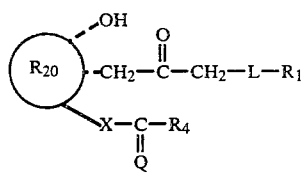

or a mixture comprising that compound and the enantiomer thereof
wherein $R_{20}$ is

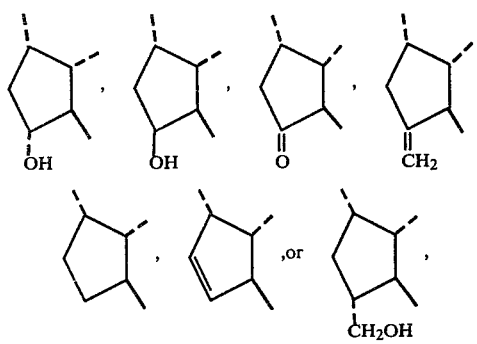

wherein L is
(1) —$(CH_2)_d$—$C(R_2)_2$—
(2) —$CH_2$—O—$CH_2$—Y— or
(3) —$CH_2CH=CH$— wherein d is zero to 5, $R_2$ is hydrogen, methyl, or fluoro, being the same or different with the proviso that one $R_2$ is not methyl when the other is fluoro, and y is a valence bond, —$CH_2$— or —$(CH_2)_2$—, wherein Q is

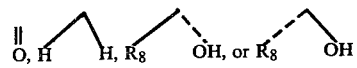

wherein $R_8$ is hydrgen or alkyl of one to 4 carbon atoms, inclusive,
wherein $R_1$ is
(1) —$COOR_3$
(2) —$CH_2OH$
(3) —$CH_2N(R_9)(R_{18})$ or

(4)

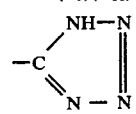

(5)

wherein $R_8$ is (a) hydrogen, (b) alkyl of one to 12 carbon atoms, inclusive, (c) cycloalkyl of 3 to 10 carbon atoms, inclusive, (d) aralkyl of 7 to 12 carbon atoms, inclusive, (e) phenyl, (f) phenyl substituted with one, 2, or 3 chloro or alkyl of one to 4 carbon atoms, inclusive,

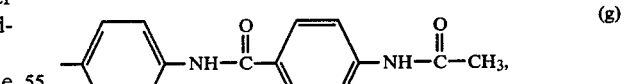 (g)

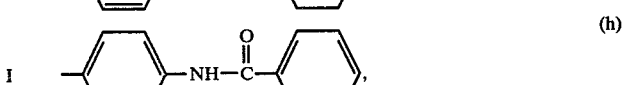 (h)

 (i)

 (j)

-continued $$-\underset{}{\bigcirc}-CH=N-NH-\overset{O}{\underset{\|}{C}}-NH_2,\quad (k)$$

(l)

[naphthyl structure]

$$-\overset{}{\underset{R_{11}}{\overset{|}{C}H}}-\overset{O}{\underset{\|}{C}}-R_{10},\quad (m)$$

wherein $R_{10}$ is phenyl, p-bromophenyl, p-biphenylyl, p-nitrophenyl, p-benzamidophenyl, or 2-naphthyl, and wherein $R_{11}$ is hydrogen or benzoyl, or (n) a pharmacologically acceptable cation, wherein $R_8$ is hydrogen, methyl, or ethyl, and $R_{18}$ is hydrogen, alkyl of one to 4 carbon atoms, inclusive, aralkyl of 7 to 12 carbon atoms, inclusive, phenyl, or phenyl substituted with alkyl of one to 4 carbon atoms, inclusive;

wherein $R_4$ is $$-\overset{R_5}{\underset{R_6}{\overset{|}{\underset{|}{C}}}}-C_gH_{2g}-CH_3 \quad (1)$$

$$-\overset{R_5}{\underset{R_6}{\overset{|}{\underset{|}{C}}}}-Z-\underset{}{\bigcirc}(T)_s \quad \text{or} \quad (2)$$

$$-CH_2\diagdown\underset{H}{\overset{}{C}}=\underset{H}{\overset{}{C}}\diagup CH_2CH_3 \quad (3)$$

wherein $C_gH_{2g}$ is alkylene of one to 9 carbon atoms, inclusive, with one to 5 carbon atoms, inclusive, in the chain between —$CR_5R_6$— and terminal methyl, wherein $R_5$ and $R_6$ are hydrogen, alkyl of one to 4 carbon atoms, inclusive, or fluoro, being the same or different, with the proviso that one of $R_5$ and $R_6$ is fluoro only when the other is hydrogen or fluoro and the further proviso that neither $R_5$ nor $R_6$ is fluoro when Z is oxa (—O—); wherein Z represents an oxa atom (—O—) or $C_jH_{2j}$ wherein $C_jH_{2j}$ is a valence bond or alkylene of one to 9 carbon atoms, inclusive, with one to 6 carbon atoms, inclusive between $CR_5R_6$- and the phenyl ring; wherein T is alkyl of one to 4 carbon atoms, inclusive, fluoro, chloro, trifluoromethyl, or —$OR_7$— wherein $R_7$ is alkyl of one to 4 carbon atoms, inclusive, and s is zero, one, 2 or 3, with the proviso that not more than two T's are other than alkyl and when s is 2 or 3 the T's are either the same or different; and wherein X is
(1) trans-CH=CH-
(2) cis-CH=CH-
(3) —C≡C— or
(4) —CH₂CH₂—;

including the lower alkanoates thereof.

When $R_4$ in the compounds of formula I is $$-\overset{R_5}{\underset{R_6}{\overset{|}{\underset{|}{C}}}}-Z-\underset{}{\bigcirc}(T)_s$$

it is preferred that "s" be either zero or one. When "s" is not zero, it is preferred that T be methyl, chloro, fluoro, trifluoromethyl, or methoxy with meta or para attachment to the phenyl ring. When Z is oxa (—O—), it is preferred that $R_5$ and $R_6$ be hydrogen, methyl, or ethyl, being the same or different. It is further preferred, when $R_5$ and $R_6$ are not hydrogen, that both $R_5$ and $R_6$ be methyl. When Z is $C_jH_{2j}$, it is preferred that $C_jH_{2j}$ be a valence bond, methylene, or ethylene. It is especially preferred that $R_4$ be $$-CH_2-O-\underset{}{\bigcirc} \quad \text{or}$$

$$-C_2H_4-\underset{}{\bigcirc}.$$

I claim:
1. A compound of the formula

[structure with $R_{20}$ ring, —CH, —CH₂—C(=O)—CH₂—L—COOR₃, X—C(=Q)—R₄]

or a mixture comprising that compound and the enantiomer thereof wherein $R_{20}$ is

[six cyclopentane ring structures with substituents: OH, OH, O, =CH₂, (ene), CH₂OH]

wherein L is
(1) —(CH₂)$_d$—C(R₂)₂—
(2) —CH₂—O—CH₂—Y— or
(3) —CH₂CH=CH— wherein d is zero to 5, $R_2$ is hydrogen, methyl, or fluoro, being the same or different with the proviso that one $R_2$ is not methyl when the other is fluoro, and Y is a valence bond, —CH₂— or —(CH₂)₂—, wherein Q is

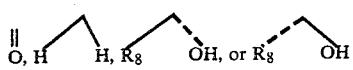

wherein $R_8$ is hydrogen or alkyl of one to 4 carbon atoms, inclusive, wherein $R_3$ is (a) hydrogen, (b) alkyl of one to 12 carbon atoms, inclusive, (c) cycloalkyl of 3 to 10 carbon atoms, inclusive, (d) aralkyl of 7 to 12 carbon atoms, inclusive, (e) phenyl, (f) phenyl substituted with one, 2, or 3 chloro or alkyl of one to 4 carbon atoms, inclusive,

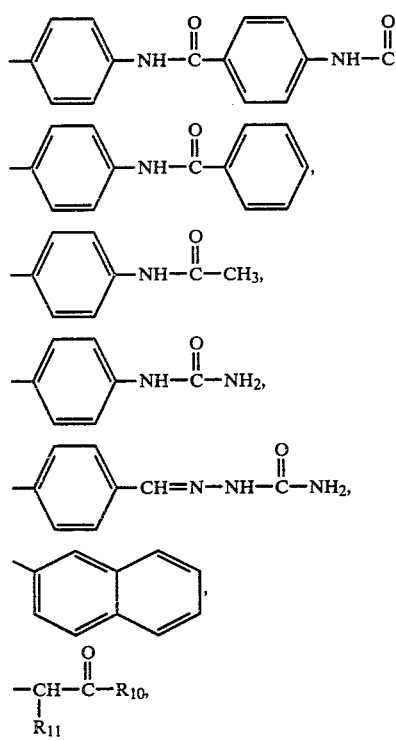

(g)

(h)

(i)

(j)

(k)

(l)

(m)

wherein $R_{10}$ is phenyl, p-bromophenyl, p-biphenylyl, p-nitrophenyl, p-benzamidophenyl, or 2-naphthyl, and wherein $R_{11}$ is hydrogen or benzoyl, or (n) a pharmacologically acceptable cation, wherein $R_4$ is

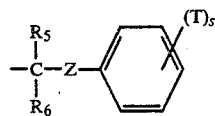

wherein $R_5$ and $R_6$ are hydrogen, alkyl of one to 4 carbon atoms, inclusive, or fluoro, being the same or different, with the proviso that one of $R_5$ and $R_6$ is fluoro only when the other is hydrogen or fluoro and the further proviso that neither $R_5$ nor $R_6$ is fluoro when Z is oxa (—O—); wherein Z represents an oxa atom (—O—) or $C_jH_{2j}$ wherein $C_jH_{2j}$ is a valence bond or alkylene of one to 9 carbon atoms, inclusive, with one to 6 carbon atoms, inclusive between $CR_5R_6$- and the phenyl ring; wherein T is alkyl of one to 4 carbon atoms, inclusive, fluoro, chloro, trifluoromethyl, or —$OR_7$— wherein $R_7$ is alkyl of one to 4 carbon atoms, inclusive, and s is zero, one, 2 or 3, with the proviso that not more than two T's are other than alkyl and when s is 2 or 3 the T's are either the same or different; and wherein X is
(1) trans-CH=CH-
(2) cis-CH=CH-
(3) -C≡C- or
(4) -CH$_2$CH$_2$—;
including the lower alkanoates thereof.

2. A compound according to claim 1 wherein $R_{20}$ is

3. A compound according to claim 1 wherein $R_{20}$ is

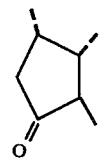

4. A compound according to claim 1 wherein $R_{20}$ is

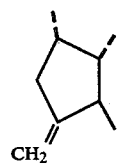

5. A compound according to claim 1 wherein $R_{20}$ is

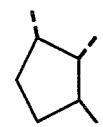

6. A compound according to claim 1 wherein $R_{20}$ is

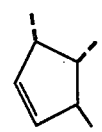

7. A compound according to claim 1 wherein $R_{20}$ is

8. A compound according to claim 1 wherein R₂₀ is

wherein L is -(CH₂)ₙ, n being 3, 4, or 5, wherein Q is

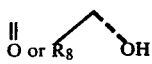

wherein R₈ is limited to hydrogen, methyl, or ethyl, and wherein R₄ is

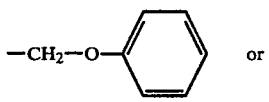 or

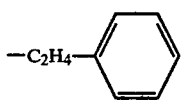

9. A compound according to claim 8 wherein X is —C≡C—.

10. A compound according to claim 8 wherein X is —CH₂CH₂—.

11. A compound according to claim 8 wherein X is trans—CH═CH—.

12. A compound according to claim 11 wherein R₃ is

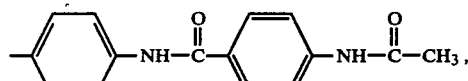

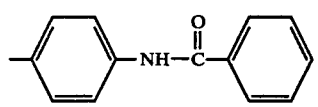

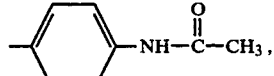

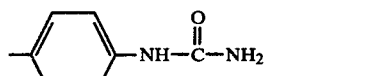

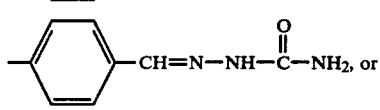

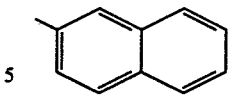

13. A compound according to claim 11 wherein R₃ is

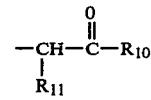

wherein R₁₀ and R₁₁ are as defined in claim 1.

14. A compound according to claim 11 wherein R₃ is hydrogen, alkyl of one to 12 carbon atoms, inclusive, or a pharmacologically acceptable cation.

15. A compound according to claim 14 wherein R₃ is hydrogen, methyl, or a pharmacologically acceptable cation.

16. 6-Keto-17-phenyl-18,19,20-trinor-PGF₁α, methyl ester, a compound according to claim 15.

17. 6-Keto-16-phenoxy-17,18,19,20-tetranor-PGF₁α, methyl ester, a compound according to claim 15.

18. 6-Keto-17-phenyl-18,19,20-trinor-13,14-dihydro-PGF₁α, methyl ester, a compound according to claim 10.

19. 6-Keto-16-phenoxy-17,18,19,20-tetranor-13,14-dihydro-PGF₁α, methyl ester, a compound according to claim 10.

20. 6-Keto-17-phenyl-18,19,20-trinor-13,14-didehydro-PGF₁α, methyl ester, a compound according to claim 9.

21. 6-Keto-16-phenoxy-17,18,19,20-tetranor-13,14-didehydro-PGF₁α, methyl ester, a compound according to claim 9.

22. 6-Keto-17-phenyl-18,19,20-trinor-cis-13-PGF₁α, methyl ester, a compound according to claim 9.

23. 6-Keto-16-phenoxy-17,18,19,20-tetranor-cis-13-PGF₁α, methyl ester, a compound according to claim 9.

24. 6-Keto-17-(m-trifluoromethylphenyl)-18,19,20-trinor-PGF₁α, methyl ester, a compound according to claim 1.

25. 6-Keto-17-(m-chlorophenyl)-18,19,20-trinor-PGF₁α, methyl ester, a compound according to claim 1.

26. 6-Keto-17-(p-fluorophenyl)-18,19,20-trinor-PGF₁α, methyl ester, a compound according to claim 1.

27. 6-Keto-16,16-dimethyl-17-phenyl-18,19,20-trinor-PGF₁α, methyl ester, a compound according to claim 1.

28. 6-Keto-16,16-difluoro-17-phenyl-18,19,20-trinor-PGF₁α, methyl ester, a compound according to claim 1.

29. 6-Keto-16-(m-trifluoromethylphenoxy)-17,18,19,20-tetranor-PGF₁α, methyl ester, a compound according to claim 1.

30. 6-Keto-16-(m-chlorophenoxy)-17,18,19,20-tetranor-PGF₁α, methyl ester, a compound according to claim 1.

31. 6-Keto-16-(p-fluorophenoxy)-17,18,19,20-tetranor-PGF₁α, methyl ester, a compound according to claim 1.

32. 6-Keto-16-methyl-16-phenoxy-18,19,20-trinor-PGF₁α, methyl ester, a compound according to claim 1.

33. 6-Keto-17-(m-trifluoromethylphenyl)-18,19,20-trinor-13,14-didehydro-PGF₁α, methyl ester, a compound according to claim 1.

34. 6-Keto-17-(m-chlorophenyl)-18,19,20-trinor-13,14-didehydro-PGF$_1\alpha$, methyl ester, a compound according to claim 1.

35. 6-Keto-17-(p-fluorophenyl)-18,19,20-trinor-13,14-didehydro-PGF$_1\alpha$, methyl ester, a compound according to claim 1.

36. 6-Keto-16,16-dimethyl-17-phenyl-18,19,20-trinor-13,14-didehydro-PGF$_1\alpha$, methyl ester, a compound according to claim 1.

37. 6-Keto-16-difluoro-17-phenyl-18,19,20-trinor-13,14-didehydro-PGF$_1\alpha$, methyl ester, a compound according to claim 1.

38. 6-Keto-16-(m-trifluoromethylphenoxy)-17,18,19,20-tetranor-13,14-didehydro-PGF$_1\alpha$, methyl ester, a compound according to claim 1.

39. 6-Keto-16-(m-chlorophenoxy)-17,18,19,20-tetranor-13,14-didehydro-PGF$_1\alpha$, methyl ester, a compound according to claim 1.

40. 6-Keto-16-methyl-16-phenoxy-18,19,20-trinor-13,14-didehydro-PGF$_1\alpha$, methyl ester, a compound according to claim 1.

41. 6-Keto-17-(m-trifluoromethylphenyl)-18,19,20-trinor-13,14-dihydro-PGF$_1\alpha$, methyl ester, a compound according to claim 1.

42. 6-Keto-17-(m-chlorophenyl)-18,19,20-trinor-13,14-dihydro-PGF$_1\alpha$, methyl ester, a compound according to claim 1.

43. 6-Keto-17-(p-fluorophenyl)-18,19,20-trinor-13,14-dihydro-PGF$_1\alpha$, methyl ester, a compound according to claim 1.

44. 6-Keto-16,16-dimethyl-17-phenyl-18,19,20-trinor-13,14-dihydro-PGF$_1\alpha$, methyl ester, a compound according to claim 1.

45. 6-Keto-16,16-difluoro-17-phenyl-18,19,20-trinor-13,14-dihydro-PGF$_1\alpha$, methyl ester, a compound according to claim 1.

46. 6-Keto-16-(m-trifluoromethylphenoxy)-17,18,19,20-tetranor-13,14-dihydro-PGF$_1\alpha$, methyl ester, a compound according to claim 1.

47. 6-Keto-16-(m-chlorophenoxy)-17,18,19,20-tetranor-13,14-dihydro-PGF$_1\alpha$, methyl ester, a compound according to claim 1.

48. 6-Keto-16-(p-fluorophenoxy)-17,18,19,20-tetranor-13,14-dihydro-PGF$_1\alpha$, methyl ester, a compound according to claim 1.

49. 6-Keto-16-methyl-16-phenoxy-18,19,20-trinor-13,14-dihydro-PGF$_1\alpha$, methyl ester, a compound according to claim 1.

50. 6-Keto-17-(m-trifluoromethylphenyl)-18,19,20-trinor-cis-13-PGF$_1\alpha$, methyl ester, a compound according to claim 1.

51. 6-Keto-17-(m-chlorophenyl)-18,19,20-trinor-cis-13-PGF$_1\alpha$, methyl ester, a compound according to claim 1.

52. 6-Keto-17-(p-fluorophenyl)-18,19,20-trinor-cis-13-PGF$_1\alpha$, methyl ester, a compound according to claim 1.

53. 6-Keto-16,16-dimethyl-17-phenyl-18,19,20-trinor-cis-13-PGF$_1\alpha$, methyl ester, a compound according to claim 1.

54. 6-Keto-16,16-difluoro-17-phenyl-18,19,20-trinor-cis-13-PGF$_1\alpha$, methyl ester, a compound according to claim 1.

55. 6-Keto-16-(m-trifluoromethylphenoxy)-17,18,19,20-tetranor-cis-13-PGF$_1\alpha$, methyl ester, a compond according to claim 1.

56. 6-Keto-16-(m-chlorophenoxy)-17,18,19,20-tetranor-cis-13-PGF$_1\alpha$, methyl ester, a compound according to claim 1.

57. 6-Keto-16-(p-fluorophenoxy)-17,18,19,20-tetranor-cis-13-PGF$_1\alpha$, methyl ester, a compound according to claim 1.

58. 6-Keto-16-methyl-16-phenoxy-18,19,20-trinor-cis-13-PGF$_1\alpha$, methyl ester, a compound according to claim 1.

59. 6-Keto-2,2-difluoro-17-phenyl-18,19,20-trinor-PGF$_1\alpha$, methyl ester, a compound according to claim 1.

60. 6-Keto-2,2-difluoro-17-(m-trifluoromethylphenyl)-18,19,20-trinor-PGF$_1\alpha$, methyl ester, a compound according to claim 1.

61. 6-Keto-2,2-difluoro-17-(m-chlorophenyl)-18,19,20-trinor-PGF$_1\alpha$, methyl ester, a compound according to claim 1.

62. 6-Keto-2,2-difluoro-17-(p-fluorophenyl)-18,19,20-trinor-PGF$_1\alpha$, methyl ester, a compound according to claim 1.

63. 6-Keto-2,2-difluoro-16,16-methyl-17-phenyl-18,19,20-trinor-PGF$_1\alpha$, methyl ester, a compound according to claim 1.

64. 6-Keto-2,2-difluoro-16,16-difluoro-17-phenyl-18,19,20-trinor-PGF$_1\alpha$, methyl ester, a compound according to claim 1.

65. 6-Keto-2,2-difluoro-16-phenoxy-17,18,19,20-tetranor-PGF$_1\alpha$, methyl ester, a compound according to claim 1.

66. 6-Keto-2,2-difluoro-16-(m-trifluoromethylphenoxy)-17,18,19,20-tetranor-PGF$_1\alpha$, methyl ester, a compound according to claim 1.

67. 6-Keto-2,2-difluoro-16-(m-chlorophenoxy)-17,18,19,20-tetranor-PGF$_1\alpha$, methyl ester, a compound according to claim 1.

68. 6-Keto-2,2-difluoro-16-(p-fluorophenoxy(-17,18,19,20-tetranor-PGF$_1\alpha$, methyl ester, a compound according to claim 1.

69. 6-Keto-2,2-difluoro-16-methyl-16-phenoxy-18,19,20-trinor-PGF$_1\alpha$, methyl ester, a compound according to claim 1.

70. 6-Keto-2,2-difluoro-17-phenyl-18,19,20-trinor-13,14-didehydro-PGF$_1\alpha$, methyl ester, a compound according to claim 1.

71. 6-Keto-2,2-difluoro-17-(m-trifluoromethylphenyl)-18,19,20-trinor-13,14-didehydro-PGF$_1\alpha$, methyl ester, a compound according to claim 1.

72. 6-Keto-2,2-difluoro-17-(m-chlorophenyl)-18,19,20-trinor-13,14-didehydro-PGF$_1\alpha$, methyl ester, a compound according to claim 1.

73. 6-Keto-2,2-difluoro-17-(p-fluorophenyl)-18,19,20-trinor-13,14-didehydro-PGF$_1\alpha$, methyl ester, a compound according to claim 1.

74. 6-Keto-2,2-difluoro-16,16-dimethyl-17-phenyl-18,19,20-trinor-13,14-didehydro-PGF$_1\alpha$, methyl ester, a compound according to claim 1.

75. 6-Keto-2,2,16,16-tetrafluoro-17-phenyl-18,19,20-trinor-13,14-didehydro-PGF$_1\alpha$, methyl ester, a compound according to claim 1.

76. 6-Keto-2,2-difluoro-16-phenoxy-17,18,19,20-tetranor-13,14-didehydro-PGF$_1\alpha$, methyl ester, a compound according to claim 1.

77. 6-Keto-2,2-difluoro-16-(m-trifluoromethylphenoxy)-17,18,19,20-tetranor-13,14-didehydro-PGF$_1\alpha$, methyl ester, a compound according to claim 1.

78. 6-Keto-2,2-difluoro-16-(m-chlorophenoxy)-17,18,19m20-tetranor-13,14-didehydro-PGF$_1\alpha$, methyl ester, a compound according to claim 1.

79. 6-Keto-2,2-difluoro-16-methyl-16-phenoxy-18,19,20-trinor-13,14-didehydro-PGF$_1\alpha$, methyl ester, a compound according to claim 1.

80. 6-Keto-2,2-difluoro-17-phenyl-18,19,20-trinor-13,14-dihydro-PGF$_1\alpha$, methyl ester, a compound according to claim 1.

81. 6-Keto-2,2-difluoro-17-(m-trifluoromethylphenyl)-18,19,20-trinor-13,14-dihydro-PGF$_1\alpha$, methyl ester, a compound according to claim 1.

82. 6-Keto-2,2-difluoro-17-(m-chlorophenyl)-18,19,20-trinor-13,14-dihydro-PGF$_1\alpha$, methyl ester, a compound according to claim 1.

83. 6-Keto-2,2-difluoro-17-(p-fluorophenyl)-18,19,20-trinor-13,14-dihydro-PGF$_1\alpha$, methyl ester, a compound according to claim 1.

84. 6-Keto-2,2-difluoro-16,16-dimethyl-17-phenyl-18,19,20-trinor-13,14-dihydro-PGF$_1\alpha$, methyl ester, a compound according to claim 1.

85. 6-Keto-2,2,16,16-Tetrafluoro-17-phenyl-18,19,20-trinor-13,14-dihydro-PGF$_1\alpha$, methyl ester, a compound according to claim 1.

86. 6-Keto-2,2-difluoro-16-phenoxy-17,18,19,20-tetranor-13,14-dihydro-PGF$_1\alpha$, methyl ester, a compound according to claim 1.

87. 6-Keto-2,2-difluoro-16-(m-trifluoromethylphenoxy)-17,18,19,20-tetranor-13,14-dihydro-PGF$_1\alpha$, methyl ester, a compound according to claim 1.

88. 6-Keto-2,2-difluoro-16-(m-chlorophenoxy)-17,18,19,20-tetranor-13,14-dihydro-PGF$_1\alpha$, methyl ester, a compound according to claim 1.

89. 6-Keto-2,2-difluoro-16-(p-fluorophenoxy)-17,18,19,20-tetranor-13,14-dihydro-PGF$_1\alpha$, methyl ester, a compound according to claim 1.

90. 6-Keto-2,2-difluoro-16-methyl-16-phenoxy-18,19,20-trinor-13,14-dihydro-PGF$_1\alpha$, methyl ester, a compound according to claim 1.

91. 6-Keto-2,2-difluoro-17-phenyl-18,19,20-trinor-cis-13-PGF$_1\alpha$, methyl ester, a compound according to claim 1.

92. 6-Keto-2,2-difluoro-17-(m-trifluoromethylphenyl)-18,19,20-trinor-cis-13-PGF$_1\alpha$, methyl ester, a compound according to claim 1.

93. 6-Keto-2,2-difluoro-17-(m-chlorophenyl)-18,19,20-trinor-cis-13-PGF$_1\alpha$, methyl ester, a compound according to claim 1.

94. 6-Keto-2,2-difluoro-17-(p-fluorophenyl)-18,19,20-trinor-cis-13-PGF$_1\alpha$, methyl ester, a compound according to claim 1.

95. 6-Keto-2,2-difluoro-16,16-dimethyl-17-phenyl-18,19,20-trinor-cis-13-PGF$_1\alpha$, methyl ester, a compound according to claim 1.

96. 6-Keto-2,2-difluoro-16,16-difluoro-17-phenyl-18,19,20-trinor-cis-13-PGF$_1\alpha$, methyl ester, a compound according to claim 1.

97. 6-Keto-2,2-difluoro-16-phenoxy-17,18,19,20-tetranor-cis-13-PGF$_1\alpha$, methyl ester, a compound according to claim 1.

98. 6-Keto-2,2-difluoro-16-(m-trifluoromethylphenoxy)-17,18,19,20-tetranor-cis-13-PGF$_1\alpha$, methyl ester, a compound according to claim 1.

99. 6-Keto-2,2-difluoro-16-(m-chlorophenoxy)-17,18,19,20-tetranor-cis-13-PGF$_1\alpha$, methyl ester, a compund according to claim 1.

100. 6-Keto-2,2-difluoro-16-(p-fluorophenoxy)-17,18,19,20-tetranor-cis-13-PGF$_1\alpha$, methyl ester, a compound according to claim 1.

101. 6-Keto-2,2-difluoro-16-methyl-16-phenoxy-18,19,20-trinor-cis-13-PGF$_1\alpha$, methyl ester, a compound according to claim 1.

102. 6-Keto-3-oxa-17-phenyl-18,19,20-trinor-PGF$_1\alpha$, methyl ester, a compound according to claim 1.

103. 6-Keto-3-oxa-17-(m-trifluoromethylphenyl)-18,19,20,-trinor-PGF$_1\alpha$, methyl ester, a compound according to claim 1.

104. 6-Keto-3-oxa-17-(m-chlorophenyl)-18,19,20,-trinor-PGF$_1\alpha$, methyl ester, a compound according to claim 1.

105. 6-Keto-3-oxa-17-(p-fluorophenyl)-18,19,20-trinor-PGF$_1\alpha$, methyl ester, a compound according to claim 1.

106. 6-Keto-3-oxa-16,16-dimethyl-17-phenyl-18,19,20-trinor-PGF$_1\alpha$, methyl ester, a compound according to claim 1.

107. 6-Keto-3-oxa-16,16-difluoro-17-phenyl-18,19,20-trinor-PGF$_1\alpha$, methyl ester, a compound according to claim 1.

108. 6-Keto-3-oxa-16-phenoxy-17,18,19,20-tetranor-PGF$_1\alpha$, methyl ester, a compound according to claim 1.

109. 6-Keto-3-oxa-16-(m-trifluoromethylphenoxy)-17,18,19,20-tetranor-PGF$_1\alpha$, methyl ester, a compound according to claim 1.

110. 6-Keto-3-oxa-16-(m-chlorophenoxy)-17,18,19,20-tetranor-PGF$_1\alpha$, methyl ester, a compound according to claim 1.

111. 6-Keto-3-oxa-16-(p-fluorophenoxy)-17,18,19,20-tetranor-PGF$_1\alpha$, methyl ester, a compound according to claim 1.

112. 6-Keto-3-oxa-16-methyl-16-phenoxy-18,19,20-trinor-PGF$_1\alpha$, methyl ester, a compound according to claim 1.

113. 6-Keto-3-oxa-17-phenyl-18,19,20-trinor-13,14-didehydro-PGF$_1\alpha$, methyl ester, a compound according to claim 1.

114. 6-Keto-3-oxa-17-(m-trifluoromethylphenyl)-18,19,20-trinor-13,14-didehydro-PGF$_1\alpha$, methyl ester, a compound according to claim 1.

115. 6-Keto-3-oxa-17-(m-chlorophenyl)-18,19,20-trinor-13,14-didehydro-PGF$_1\alpha$, methyl ester, a compound according to claim 1.

116. 6-Keto-3-oxa-17-(p-fluorophenyl)-18,19,20-trinor-13,14-didehydro-PGF$_1\alpha$, methyl ester, a compound according to claim 1.

117. 6-Keto-3-oxa-16,16-dimethyl-17-phenyl-18,19,20-trinor-13,14-didehydro-PGF$_1\alpha$, methyl ester, a compound according to claim 1.

118. 6-Keto-3-oxa-16,16-difluoro-17-phenyl-18,19,20-trinor-13,14-didehydro-PGF$_1\alpha$, methyl ester, a compound according to claim 1.

119. 6-Keto-3-oxa-16-phenoxy-17,18,19,20-tetranor-13,14-didehydro-PGF$_1\alpha$, methyl ester, a compound according to claim 1.

120. 6-Keto-3-oxa-16-(m-trifluoromethylphenoxy)-17,18,19,20-tetranor-13,14-didehydro-PGF$_1\alpha$, methyl ester, a compound according to claim 1.

121. 6-Keto-3-oxa-16-(m-chlorophenoxy)-17,18,19,20-tetranor-13,14-didehydro-PGF$_1\alpha$, methyl ester, a compound according to claim 1.

122. 6-Keto-3-oxa-16-methyl-16-phenoxy-18,19,20-trinor-13,14-didehydro-PGF$_1\alpha$, methyl ester, a compound according to claim 1.

123. 6-Keto-3-oxa-17-phenyl-18,19,20-trinor-13,14-dihydro-PGF$_1\alpha$, methyl ester, a compound according to claim 1.

124. 6-Keto-3-oxa-17-(m-trifluoromethylphenyl)-18,19,20-trinor-13,14-dihydro-PGF$_1\alpha$, methyl ester, a compound according to claim 1.

125. 6-Keto-3-oxa-17-(m-chlorophenyl)-18,19,20-trinor-13,14-dihydro-PGF$_1\alpha$, methyl ester, a compound according to claim 1.

126. 6-Keto-3-oxa-17-(p-fluorophenyl)-18,19,20-trinor-13,14-dihydro-PGF$_1\alpha$, methyl ester, a compound according to claim 1.

127. 6-Keto-3-oxa-16,16-dimethyl-17-phenyl-18,19,20-trinor-13,14-dihydro-PGF$_1\alpha$, methyl ester, a compound according to claim 1.

128. 6-Keto-3-oxa-16,16-difluoro-17-phenyl-18,19,20-trinor-13,14-dihydro-PGF$_1\alpha$, methyl ester, a compound according to claim 1.

129. 6-Keto-3-oxa-16-phenyl-17,18,19,20-tetranor-13,14-dihydro-PGF$_1\alpha$, methyl ester, a compound according to claim 1.

130. 6-Keto-3-oxa-16-(m-trifluoromethylphenoxy)-17,18,19,20-tetranor-13,14-dihydro-PGF$_1\alpha$, methyl ester, a compound according to claim 1.

131. 6-Keto-3-oxa-16-(m-chlorophenoxy)-17,18,19,20-tetranor-13,14-dihydro-PGF$_1\alpha$, methyl ester, a compound according to claim 1.

132. 6-Keto-3-oxa-16-(p-fluorophenoxy)-17,18,19,20-tetranor-13,14-dihydro-PGF$_1\alpha$, methyl ester, a compound according to claim 1.

133. 6-Keto-3-oxa-16-methyl-16-phenoxy-18,19,20-trinor-13,14-dihydro-PGF$_1\alpha$, methyl ester, a compound according to claim 1.

134. 6-Keto-3-oxa-17-phenyl-18,19,20-trinor-cis-13-PGF$_1\alpha$, methyl ester, a compound according to claim 1.

135. 6-Keto-3-oxa-17-(m-trifluoromethylphenyl)-18,19,20-trinor-cis-13-PGF$_1\alpha$, methyl ester, a compound according to claim 1.

136. 6-Keto-3-oxa-17-(m-chlorophenyl)-18,19,20-trinor-cis-13-PGF$_1\alpha$, methyl ester, a compound according to claim 1.

137. 6-Keto-3-oxa-17-(p-fluorophenyl)-18,19,20-trinor-cis-13-PGF$_1\alpha$, methyl ester, a compound according to claim 1.

138. 6-Keto-3-oxa-16,16-dimethyl-17-phenyl-18,19,20-trinor-cis-13-PGF$_1\alpha$, methyl ester, a compound according to claim 1.

139. 6-Keto-3-oxa-16,16-difluoro-17-phenyl-18,19,20-trinor-cis-13PGF$_1\alpha$, methyl ester, a compound according to claim 1.

140. 6-Keto-3-oxa-16-phenoxy-17,18,19,20-tetranor-cis-13-PGF$_1\alpha$, methyl ester, a compound according to claim 1.

141. 6-Keto-3-oxa-16-(m-trifluoromethylphenoxy)-17,18,19,20-tetranor-cis-13-PGF$_1\alpha$, methyl ester, a compound according to claim 1.

142. 6-Keto-3-oxa-16-(m-chlorophenoxy)-17,18,19,20-tetranor-cis-13-PGF$_1\alpha$, methyl ester, a compound according to claim 1.

143. 6-Keto-3-oxa-(p-fluorophenoxy)-17,18,19,20-tetranor-cis-13-PGF$_1\alpha$, methyl ester, a compound according to claim 1.

144. 6-Keto-3-oxa-16-methyl-16-phenoxy-18,19,20-trinor-cis-13-PGF$_1\alpha$, methyl ester, a compound according to claim 1.

145. 6-Keto-17-phenyl-18,19,20-trinor-PGF$_1\alpha$, a compound according to claim 15.

* * * * *

UNITED STATES PATENT OFFICE
CERTIFICATE OF CORRECTION

Patent No. 4,215,222      Dated  29 July 1980

Inventor(s)  Udo F. Axen

It is certified that error appears in the above-identified patent and that said Letters Patent are hereby corrected as shown below:

Column 1, lines 25-29,         should read

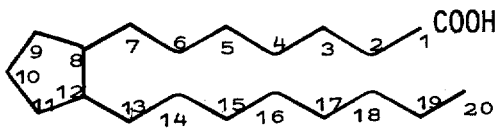      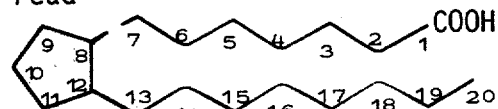

Column 2, line 46, "wherein $R_8$ is" should read -- wherein $R_3$ is --;
Column 3, line 19, "wherein $R_8$ is" should read -- wherein $R_9$ is --
Column 4, lines 32-40, that portion of the formula reading

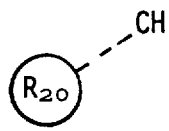      should read      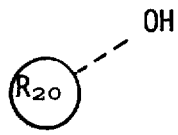

Column 4, lines 45-52, the formula reading

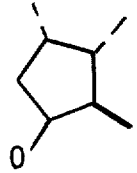      should read      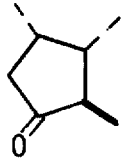

UNITED STATES PATENT OFFICE
CERTIFICATE OF CORRECTION

Patent No. 4,215,222               Dated 29 July 1980

Inventor(s) U. F. Axen

It is certified that error appears in the above-identified patent and that said Letters Patent are hereby corrected as shown below:

Column 9, line 10, "16-difluoro-" should read -- 16,16-difluoro --;
    line 68, "compond" should read -- compound --;
Column 10, line 21, "16,16-methyl-" should read -- 16,16-dimethyl --;
    line 36, "(p-fluorophenoxy(-" should read -- (p-fluorophenoxy)- --;
Column 13, line 16, "16-phenyl-" should read -- 16-phenoxy- --.

Signed and Sealed this

Twenty-sixth Day of May 1981

[SEAL]

Attest:

RENE D. TEGTMEYER

Attesting Officer      Acting Commissioner of Patents and Trademarks